United States Patent
Yasunaga

(10) Patent No.: US 9,675,402 B2
(45) Date of Patent: Jun. 13, 2017

(54) TREATMENT DEVICE FOR MEDICAL TREATMENT

(71) Applicant: OLYMPUS CORPORATION, Tokyo (JP)

(72) Inventor: Shinji Yasunaga, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 281 days.

(21) Appl. No.: 14/172,125

(22) Filed: Feb. 4, 2014

(65) Prior Publication Data

US 2014/0155877 A1    Jun. 5, 2014

Related U.S. Application Data

(63) Continuation of application No. PCT/JP2012/068612, filed on Jul. 23, 2012.

(30) Foreign Application Priority Data

Aug. 5, 2011    (JP) .................................. 2011-171750

(51) Int. Cl.
*A61B 18/10* (2006.01)
*A61B 18/14* (2006.01)
(Continued)

(52) U.S. Cl.
CPC .......... *A61B 18/10* (2013.01); *A61B 18/1445* (2013.01); *A61B 18/085* (2013.01);
(Continued)

(58) Field of Classification Search
CPC .................................................. A61B 18/085
See application file for complete search history.

(56) References Cited

U.S. PATENT DOCUMENTS

| | | | |
|---|---|---|---|
| 6,740,085 B2 * | 5/2004 | Hareyama ............ | A61B 18/085 606/50 |
| 7,329,255 B2 * | 2/2008 | McGaffigan ......... | A61B 18/085 606/41 |

(Continued)

FOREIGN PATENT DOCUMENTS

| | | |
|---|---|---|
| JP | 2001-190561 A | 7/2001 |
| JP | 2003-135480 A | 5/2003 |

(Continued)

OTHER PUBLICATIONS

International Search Report dated Aug. 14, 2012 issued in PCT/JP2012/068612.

*Primary Examiner* — Ronald Hupczey, Jr.
(74) *Attorney, Agent, or Firm* — Scully, Scott, Murphy & Presser, P.C.

(57) ABSTRACT

A treatment device for a medical treatment heats a biotissue. The device includes first and second heat transfer portions which come in contact with the biotissue. The device includes first and second resistance elements which are supplied a power having a first power value and a second power value to heat the first heat transfer portion and second heat transfer portion, respectively. The device includes temperature acquiring section which acquires a first temperature of the first heat transfer portion. The device includes a control section which calculates the first power value based on the first temperature, and determines the second power value corresponding to the first power value. The device includes first and second power supplying sections which supply the power having the first and second power value to the first and second resistance elements, respectively.

18 Claims, 12 Drawing Sheets

(51) Int. Cl.
*A61B 18/00* (2006.01)
*A61B 18/08* (2006.01)

(52) U.S. Cl.
CPC ............ *A61B 2018/00589* (2013.01); *A61B 2018/00595* (2013.01); *A61B 2018/00642* (2013.01); *A61B 2018/00702* (2013.01); *A61B 2018/00791* (2013.01); *A61B 2018/087* (2013.01); *A61B 2018/1412* (2013.01); *A61B 2018/1455* (2013.01)

(56) References Cited

U.S. PATENT DOCUMENTS

| | | | |
|---|---|---|---|
| 2003/0073987 A1* | 4/2003 | Sakurai | A61B 17/320068 606/28 |
| 2003/0125734 A1 | 7/2003 | Mollenauer | |
| 2009/0248002 A1 | 10/2009 | Takashino et al. | |
| 2012/0022516 A1* | 1/2012 | Stuebe | A61B 18/085 606/31 |

FOREIGN PATENT DOCUMENTS

| | | |
|---|---|---|
| JP | 2005-514102 A | 5/2005 |
| JP | 2009-247893 A | 10/2009 |

* cited by examiner

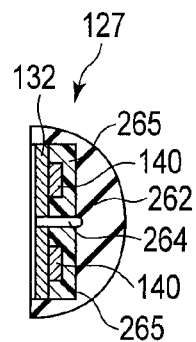
F I G. 3C
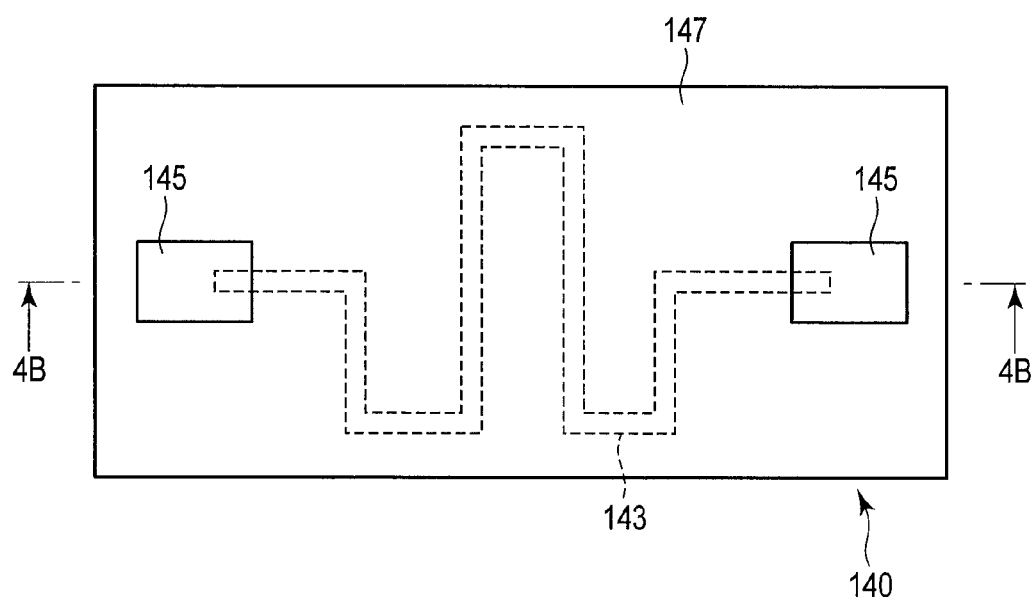
F I G. 4A

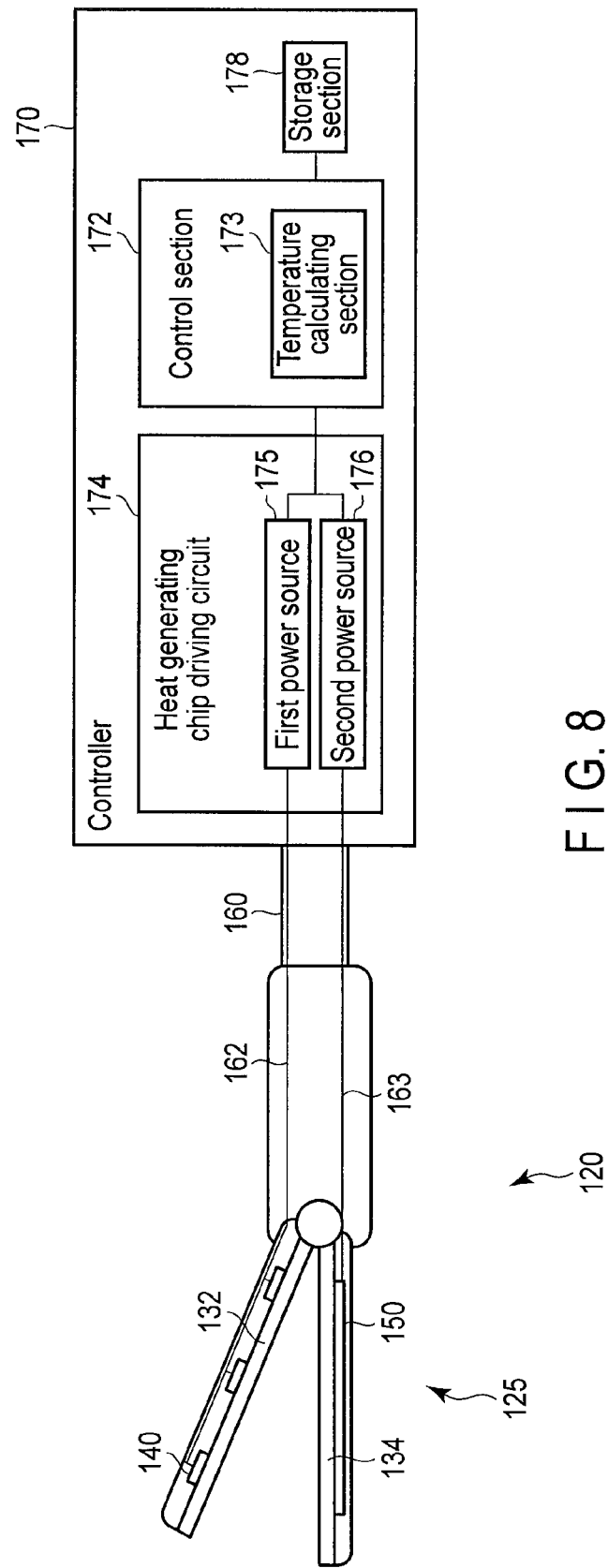
F I G. 8

TREATMENT DEVICE FOR MEDICAL TREATMENT

CROSS-REFERENCE TO RELATED APPLICATIONS

This application is a Continuation application of PCT Application No. PCT/JP2012/068612, filed Jul. 23, 2012 and based upon and claiming the benefit of priority from prior Japanese Patent Application No. 2011-171750, filed Aug. 5, 2011, the entire contents of all of which are incorporated herein by reference.

BACKGROUND OF THE INVENTION

1. Field of the Invention

The present invention relates to a treatment device for a medical treatment.

2. Description of the Related Art

In general, a treatment device for a medical treatment is known which treats a biotissue by use of heat energy. For example, in Jpn. Pat. Appln. KOKAI Publication No. 2001-190561, the following treatment device for the medical treatment is disclosed. This treatment device for the medical treatment has an openable/closable holding portion to hold a biotissue that is a treatment object. In this holding portion, a resistance element is disposed which functions as a heater to heat the holding portion. In such a treatment device for the medical treatment, the biotissue is held by the holding portion, and the biotissue of the held portion is heated, whereby the biotissue can be anastomosed. As to control of an amount of power to be supplied to the resistance element, in Jpn. Pat. Appln. KOKAI Publication No. 2001-190561, there are disclosed a control method of supplying the power of the amount of a predetermined constant value, and a method of controlling a temperature of the resistance element to a predetermined temperature by feedback control while performing temperature measurement on the basis of a change of a resistance value of the resistance element.

In use of such a treatment device for a medical treatment as described above, it is general that an area of a biotissue to be held by a holding portion during anastomosis is not constant and varies in every treatment. Consequently, in a control method in which an amount of power to be supplied to a resistance element that functions as a heater is set to a predetermined constant value, an anastomosis temperature varies in every treatment. As a result, there is the possibility that a joining strength becomes unstable. On the other hand, in a method in which the temperature of the resistance element is controlled to a predetermined temperature by feedback control while performing temperature measurement on the basis of a change of a resistance value of the resistance element, it is necessary to accurately acquire characteristics of a relation between the resistance value and the temperature of the resistance element in advance. For this purpose, it is necessary to manage uniformity of the resistance element with high precision during manufacturing, or to accurately measure the resistance-temperature characteristics of the resistance element individually. As a result, costs of the device increase disadvantageously. Furthermore, in the feedback control, the temperature control to be executed tends to be complicated.

BRIEF SUMMARY OF THE INVENTION

According to the present invention, an object is to provide a treatment device for a medical treatment which can execute sufficient temperature control while simplifying the device and control to decrease costs.

To achieve the above described object, according to an aspect of the invention, a treatment device for a medical treatment configured to heat a biotissue at a desired temperature to perform the medical treatment includes a first heat transfer portion configured to come in contact with the biotissue to transfer heat to the biotissue; a second heat transfer portion configured to move relatively to the first heat transfer portion, and hold the biotissue together with the first heat transfer portion to transfer the heat to the biotissue; a first resistance element to which a power having a first power value is supplied to heat the first heat transfer portion; a second resistance element to which a power having a second power value is supplied to heat the second heat transfer portion; a temperature acquiring section configured to acquire a temperature of the first heat transfer portion as a first temperature; a control section configured to calculate the first power value to set the first temperature to the desired temperature based on the first temperature, and determine the second power value corresponding to the first power value; a first power supplying section configured to supply the power having the first power value to the first resistance element; and a second power supplying section configured to supply the power having the second power value to the second resistance element.

According to the present invention, there can be provided a treatment device for a medical treatment which can execute sufficient temperature control while simplifying the device and control to decrease costs since a power to be supplied to a first resistance element and a power to be supplied to a second resistance element are determined on the basis of a first power value determined by feeding back a temperature of a first heat transfer portion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3C is a view schematically showing the configuration example of the first holding member of the holding portion according to the one embodiment of the present invention, and is a cross-sectional view taken along the 3C-3C line of FIG. 3A;

FIG. 4A is a top view schematically showing a configuration example of a heat generating chip according to the one embodiment of the present invention;

FIG. 8 is a view schematically showing one example of a configuration concerning a heating treatment of the treatment device for a medical treatment according to the one embodiment of the present invention;

DETAILED DESCRIPTION OF THE INVENTION

Figure 1:
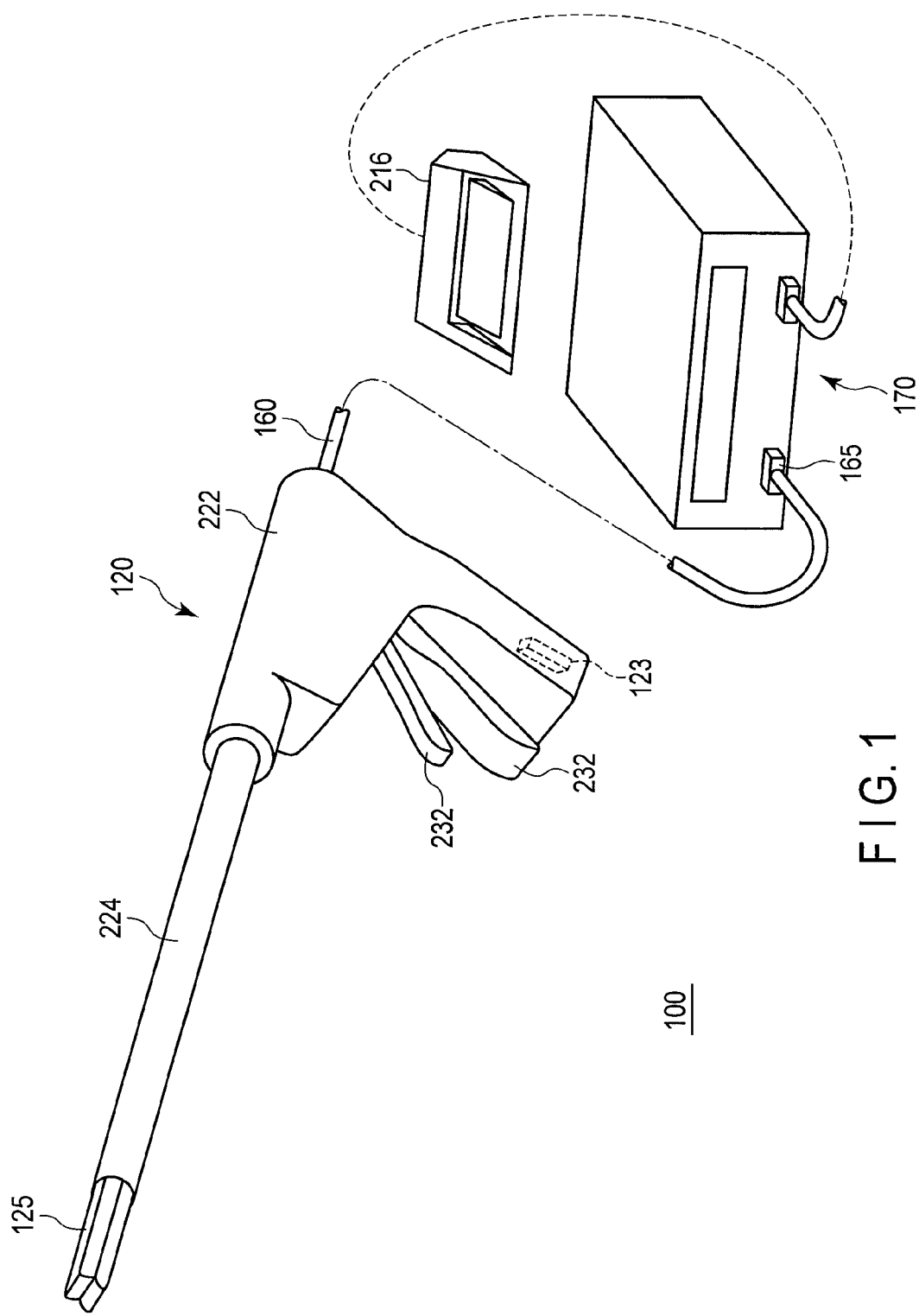
FIG. 1 is a schematic view showing a configuration example of a treatment device for a medical treatment according to one embodiment of the present invention.

One embodiment of the present invention will be described with reference to the drawings. A treatment device for a medical treatment according to the present embodiment is a device for use in the medical treatment of a biotissue, and a device which applies high frequency energy and heat energy to the biotissue. As shown in FIG. 1, a treatment device 100 for the medical treatment includes an energy treatment tool 120, a controller 170, and a foot switch 216.

The energy treatment tool 120 is a linear type treatment tool for a surgical treatment, for example, for passing through an abdominal wall to perform the treatment. The energy treatment tool 120 has a handle 222, a shaft 224 attached to the handle 222, and a holding portion 125 disposed at the tip of the shaft 224. The holding portion 125 is an openable and closable treatment portion which holds a biotissue of a treatment object, to perform a treatment such as coagulation or incision of the biotissue. Hereinafter, for explanation, a holding portion 125 side will be referred to as a distal side, and a handle 222 side will be referred to as a proximal side. The handle 222 includes operation knobs 232 to operate the holding portion 125. Moreover, a portion of the handle 222 includes a non-volatile memory 123. In the memory 123, there are stored an inherent coefficient according to the energy treatment tool 120 including a characteristics of the heat generating chip described later. It is to be noted that a shape of the energy treatment tool 120 shown herein is, needless to say, one example, and may be any shape as long as the tool has a similar function. For example, the tool may have such a shape as forceps, or the shaft may be bent.

The handle 222 is connected to the controller 170 via a cable 160. Here, the cable 160 is connected to the controller 170 by a connector 165, and this connection is detachably attached. That is, in the treatment device 100 for the medical treatment, the energy treatment tool 120 can be changed for every treatment. The controller 170 is connected to the foot switch 216. The foot switch 216 to be operated by a foot may be replaced with a switch to be operated by a hand or another switch. An operator operates a pedal of the foot switch 216, to switch ON/OFF of supply of energy from the controller 170 to the energy treatment tool 120.

Figure 2A:
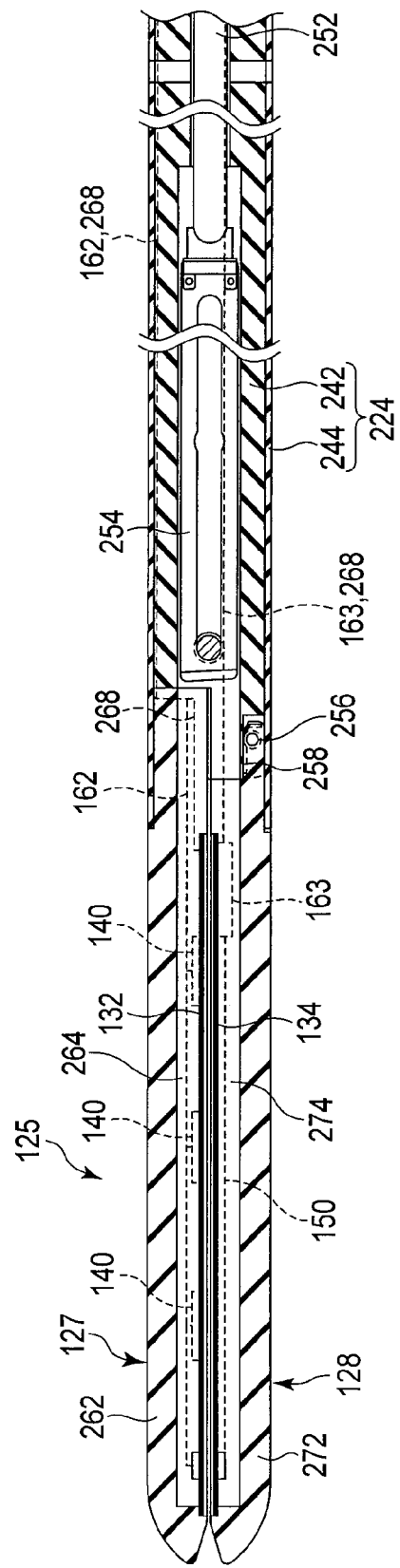
FIG. 2A is a schematic view of a cross section showing a configuration example of a shaft and a holding portion of an energy treatment tool according to the one embodiment of the present invention, and shows a state where the holding portion is closed.
Figure 2B:
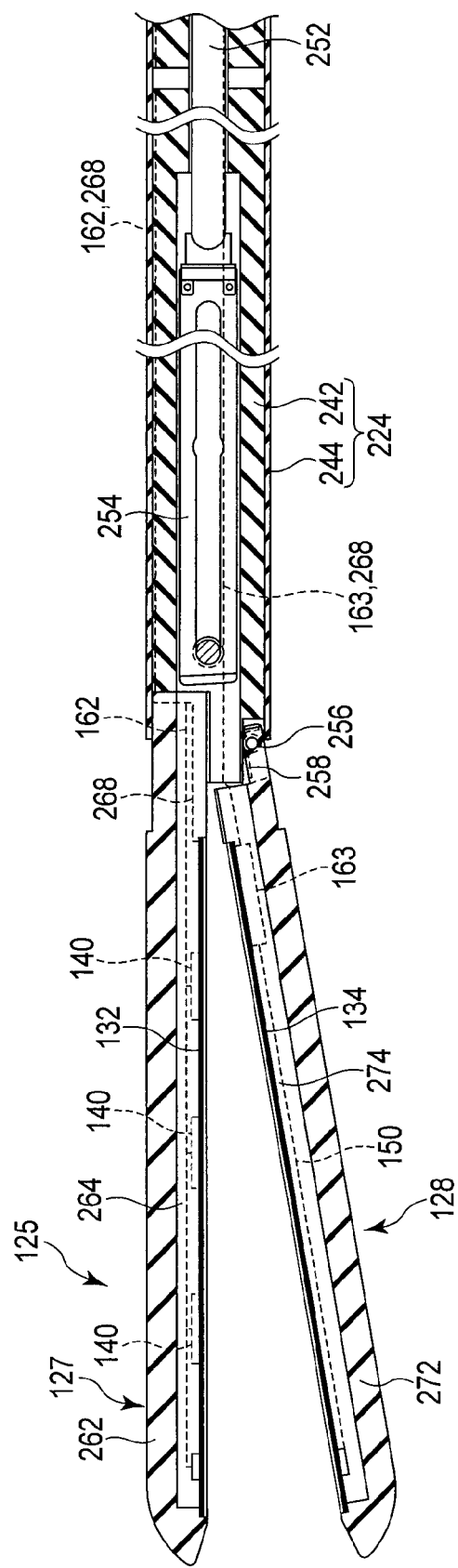
FIG. 2B is a schematic view of a cross section showing the configuration example of the shaft and the holding portion of the energy treatment tool according to the one embodiment of the present invention, and shows a state where the holding portion is opened.

One example of a structure of the holding portion 125 and the shaft 224 is shown in FIGS. 2A and 2B. FIG. 2A shows a state where the holding portion 125 is closed, and FIG. 2B shows a state where the holding portion 125 is opened. The shaft 224 includes a tubular body 242 and a sheath 244. The tubular body 242 is fixed to the handle 222 by a proximal portion of the tubular body. The sheath 244 is disposed on an outer periphery of the tubular body 242 so that the sheath is slidable along an axial direction of the tubular body 242.

In a distal portion of the tubular body 242, the holding portion 125 is disposed. The holding portion 125 includes a first holding member 127 and a second holding member 128. A proximal portion of the first holding member 127 is fixed to the distal portion of the tubular body 242 of the shaft 224. On the other hand, a proximal portion of the second holding member 128 is rotatably supported in the distal portion of the tubular body 242 of the shaft 224 by a support pin 256. Therefore, the second holding member 128 rotates around an axis of the support pin 256, and opens from the first holding member 127 and closes thereto.

In the state where the holding portion 125 is closed, a cross sectional shape of the proximal portion of the first holding member 127 which is combined with the proximal portion of the second holding member 128 is a round shape. The second holding member 128 is urged by an elastic member 258 such as a leaf spring so that the second holding member opens from the first holding member 127. When the sheath 244 is slid along the tubular body 242 to the distal side to cover, with the sheath 244, the proximal portion of the first holding member 127 and the proximal portion of the second holding member 128, the first holding member 127 and the second holding member 128 close against an urging force of the elastic member 258, as shown in FIG. 2A. On the other hand, when the sheath 244 is slid to the proximal side of the tubular body 242, the second holding member 128 opens from the first holding member 127 by the urging force of the elastic member 258, as shown in FIG. 2B.

Into the tubular body 242, there are inserted energization lines 268 for high frequency electrodes which are to be connected to a first high frequency electrode 132, described later, or a second high frequency electrode 134, described later. Further, into the tubular body 242, there are inserted energization lines 162 for heat generating chips which are to be connected to heat generating chips 140 as heat generating members, described later, and energization lines 163 for a sheet heater which are to be connected to a sheet heater 150 as a heat generating member, described later.

In the tubular body 242, a driving rod 252 connected to one of the operation knobs 232 on the proximal side thereof is movably disposed along the axial direction of the tubular body 242. On the distal side of the driving rod 252, a thin plate-like cutter 254 provided with a blade on the distal side is disposed. When the operation knob 232 is operated, the cutter 254 is moved along the axial direction of the tubular body 242 via the driving rod 252. When the cutter 254 moves to the distal side, the cutter 254 is received in later-described cutter guide grooves 264 and 274 formed in the holding portion 125.

Figure 3A:
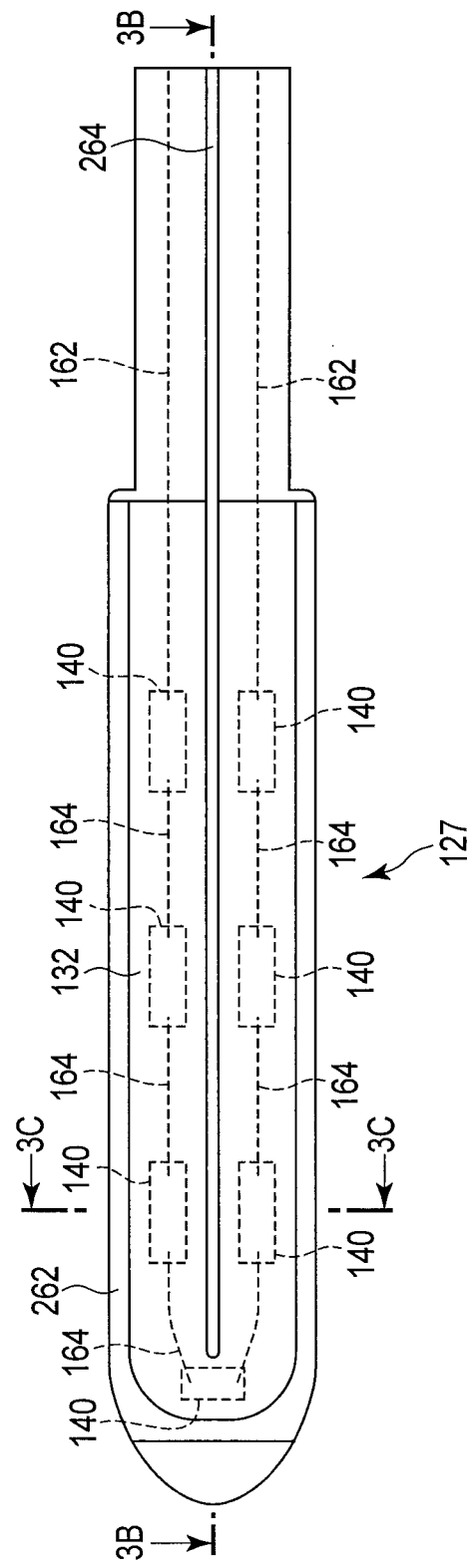
FIG. 3A is a plan view schematically showing a configuration example of a first holding member of the holding portion according to the one embodiment of the present invention.
Figure 3B:
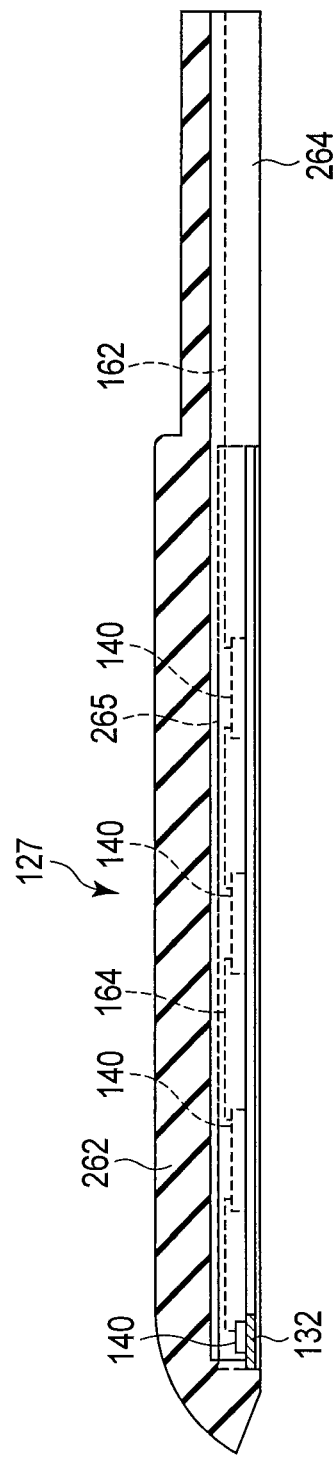
FIG. 3B is a view schematically showing the configuration example of the first holding member of the holding portion according to the one embodiment of the present invention, and is a longitudinal sectional view taken along the 3B-3B line of FIG. 3A.

The first holding member 127 has a first holding member main body 262, and the second holding member 128 has a second holding member main body 272. As shown in FIGS. 3A, 3B and 3C, in the first holding member main body 262, there is formed the cutter guide groove 264 to guide the above-mentioned cutter 254. In the first holding member main body 262, a concave portion is provided in which the first high frequency electrode 132 made of, for example, a thin plate of copper is disposed. The first high frequency electrode 132 has the cutter guide groove 264, and hence a planar shape of the electrode is substantially a U-shape as shown in FIG. 3A. As shown in FIGS. 2A and 2B, one of the energization lines 268 for the high frequency electrodes is electrically connected to the first high frequency electrode 132. The first high frequency electrode 132 is connected to the cable 160 via the energization line 268 for the high frequency electrode.

Moreover, as described later in detail, the heat generating chips 140 are joined to the surface of the first high frequency electrode 132 on the side of the first holding member main body 262. In such a manner as to cover the heat generating chips 140, wires and the like to the heat generating chips 140, and the first high frequency electrode 132, a sealant made of, for example, silicone is applied to form a sealing film 265.

The second holding member 128 has a shape symmetrical to the first holding member 127. That is, at a position of the second holding member 128 which faces the cutter guide groove 264, the cutter guide groove 274 is formed. Moreover, at a position of the second holding member main body 272 which faces the first high frequency electrode 132, the second high frequency electrode 134 is disposed. The second high frequency electrode 134 is connected to the cable 160 via the energization line 268 for the high frequency electrode. Furthermore, as described later in detail, the sheet heater 150 is joined to the surface of the second high frequency electrode 134 on the side of the second holding member main body 272.

When the closed holding portion 125 holds the biotissue, the held biotissue comes in contact with the first high frequency electrode 132 and the second high frequency electrode 134. The first holding member 127 and the second holding member 128 have mechanisms for heat generation, to cauterize the biotissue which comes in contact with the first high frequency electrode 132 and the second high frequency electrode 134. The heat generation mechanism disposed in the first holding member 127 is different from the heat generation mechanism disposed in the second holding member 128. First, the heat generation mechanism disposed in the first holding member 127 will be described.

Figure 4B:
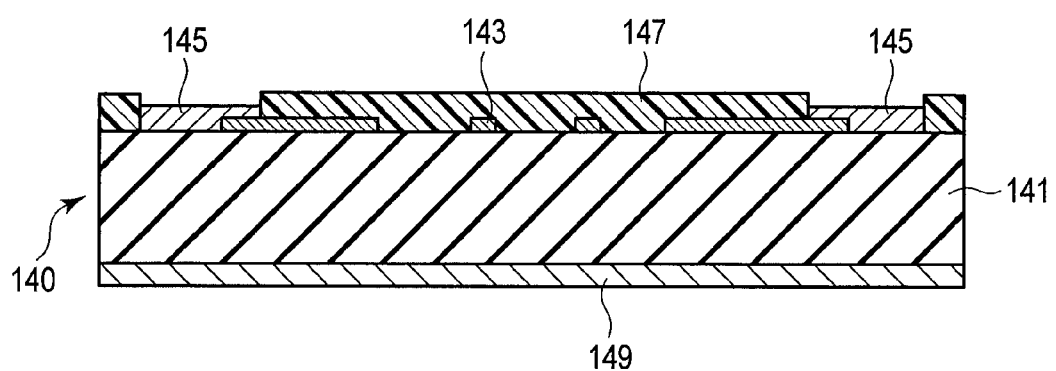
FIG. 4B is a view schematically showing the configuration example of the heat generating chip according to the one embodiment of the present invention, and is a sectional view taken along the 4B-4B line shown in FIG. 4A.

The heat generating chips 140 included in the mechanism of the heat generation of the first holding member 127 will be described with reference to FIG. 4A and FIG. 4B. Here, FIG. 4A is a top view, and FIG. 4B is a sectional view taken along the 4B-4B line shown in FIG. 4A. Each of the heat generating chips 140 is formed by using a substrate 141 made of alumina. On a front surface which is one of main surfaces of the substrate 141, there is formed a resistance pattern 143 which is a Pt thin film for the heat generation. Moreover, in the vicinities of two short sides of a rectangular shape of the front surface of the substrate 141, rectangular electrodes 145 are formed, respectively. Here, the electrodes 145 are connected to respective ends of the resistance pattern 143. On the front surface of the substrate 141 excluding portions in which the electrodes 145 are formed and including a portion on the resistance pattern 143, an insulation film 147 made of, for example, a polyimide is formed.

On the whole back surface of the substrate 141, a joining metal layer 149 is formed. The electrodes 145 and the joining metal layer 149 are multilayer films made of, for example, Ti, Cu, Ni, and Au. These electrodes 145 and the joining metal layer 149 are stable during soldering or the like. The joining metal layer 149 is disposed to stabilize the joining, for example, when the heat generating chips 140 are soldered to the first high frequency electrode 132.

The heat generating chips 140 are disposed on the surface (a second main surface) of the first high frequency electrode 132 on a side opposite to the surface (a first main surface) thereof which comes in contact with the biotissue. Here, the heat generating chips 140 are fixed, respectively, by soldering the front surface of the joining metal layer 149 to the second main surface of the first high frequency electrode 132.

Figure 5:
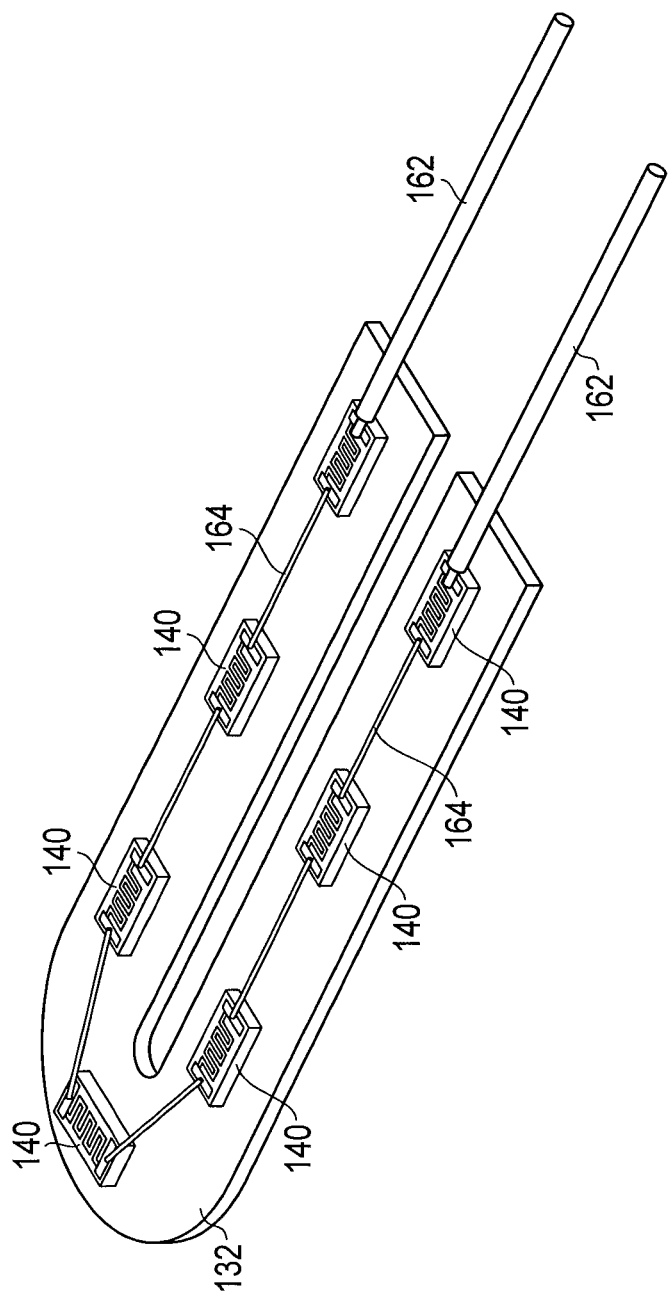
FIG. 5 is a schematic view showing a configuration example on a first high frequency electrode of the holding portion according to the one embodiment of the present invention.

The heat generating chips 140 on the first high frequency electrode 132 and a configuration concerning the connection of the chips will be described with reference to FIG. 5. On the first high frequency electrode 132, the seven heat generating chips 140 are disposed in a discrete manner. That is, the heat generating chips 140 are arranged every three chips in each of two rows symmetrically via the cutter guide groove 264 from the proximal side toward the distal side, and further the one heat generating chip 140 is disposed in a tip portion of the first high frequency electrode 132.

The resistance patterns 143 of these heat generating chips 140 are connected in series via the electrodes 145. The adjacent electrodes 145 are connected to each other by a wire 164 formed, for example, by wire bonding. Both ends of the heat generating chips connected in series are connected to a pair of energization lines 162 for the heat generating chips. The pair of energization lines 162 for the heat generating chips are connected to the cable 160. In such a manner as to cover the heat generating chips 140 and the energization lines 162 for the heat generating chips, the sealant made of, for example, silicone is applied onto the first high frequency electrode 132, whereby the sealing film 265 is formed as shown in FIGS. 3A, 3B and 3C.

In this way, the heat generating chips 140 are connected to the controller 170 via the energization lines 162 for the heat generating chips, and the cable 160. The controller 170 controls a power to be supplied to the heat generating chips 140. As described above, in the present embodiment, the heat generating chips 140 are disposed in the first high frequency electrode 132, but this disposition is for the purpose of enhancing temperature uniformity of the first high frequency electrode 132, and it can also be regarded that all the seven heat generating chips 140 electrically configure a single heat generating chip.

A current output from the controller 170 flows through the respective resistance patterns 143 of the seven heat generating chips 140. As a result, the respective resistance patterns 143 generate heat. When the resistance patterns 143 generate the heat, the heat is transferred to the first high frequency electrode 132. By this heat, the biotissue which comes in contact with the first high frequency electrode 132 is cauterized.

For efficiently transferring the heat generated in the heat generating chips 140 to the first high frequency electrode 132, each of the sealing film 265 and the first holding member main body 262 around the film preferably has a thermal conductivity lower than a thermal conductivity of the first high frequency electrode 132 or the substrate 141. The low thermal conductivity of each of the sealing film 265 and the first holding member main body 262 makes it possible to realize heat conduction with less loss.

Figure 6:
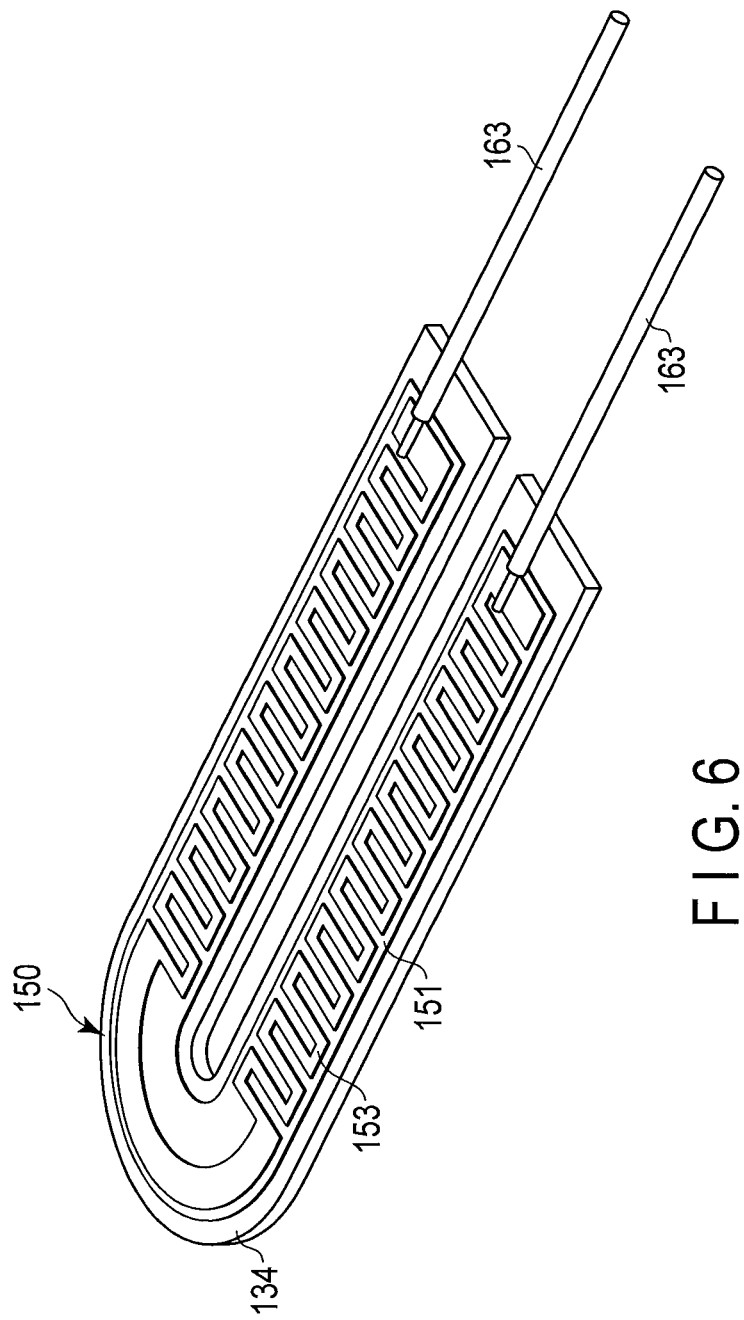
FIG. 6 is a schematic view showing a configuration example on a second high frequency electrode of the holding portion according to the one embodiment of the present invention.

Next, the heat generation mechanism disposed in the second holding member 128 will be described with reference to FIG. 6. On the second high frequency electrode 134 of the second holding member 128, the sheet heater 150 is disposed. In the sheet heater 150, a thin film-like resistor 153 is formed on a thin substrate 151 having excellent heat transfer properties.

The substrate 151 has about the same U-shape as the second high frequency electrode 134, and covers a large portion of the surface of the second high frequency electrode 134. The thin film resistor 153 is formed in such a manner as to cover a large portion of the substrate 151. The thin film resistor 153 may be formed in a pattern form as shown in FIG. 6, or may be formed without any clearances in the one surface. The thin film resistor 153 is, for example, a carbon thin film. The thin film resistor 153 of the sheet heater 150 has a resistance lower than that of the resistance patterns 143 of the heat generating chips 140, and the sheet heater 150 is inexpensive as compared with the heat generating chips 140.

The pair of energization lines 163 for the sheet heater are connected to both ends of the thin film resistor 153. The pair of energization lines 163 for the sheet heater are connected to the cable 160. In this way, the sheet heater 150 is connected to the controller 170 via the energization lines 163 for the sheet heater and the cable 160.

In such a manner as to cover the sheet heater 150 and the energization lines 163 for the sheet heater, a sealant made of, for example, silicone is applied onto the second high frequency electrode 134, whereby a sealing film is formed. This second high frequency electrode 134 is disposed in the second holding member main body 272. Here, a material and a shape of the first holding member main body 262 are equivalent to a material and a shape of the second holding member main body 272, and heat loads of these main bodies are substantially equal to each other. Therefore, heat characteristics of the first holding member 127 are substantially equal to heat characteristics of the second holding member 128 as a whole.

Figure 7:
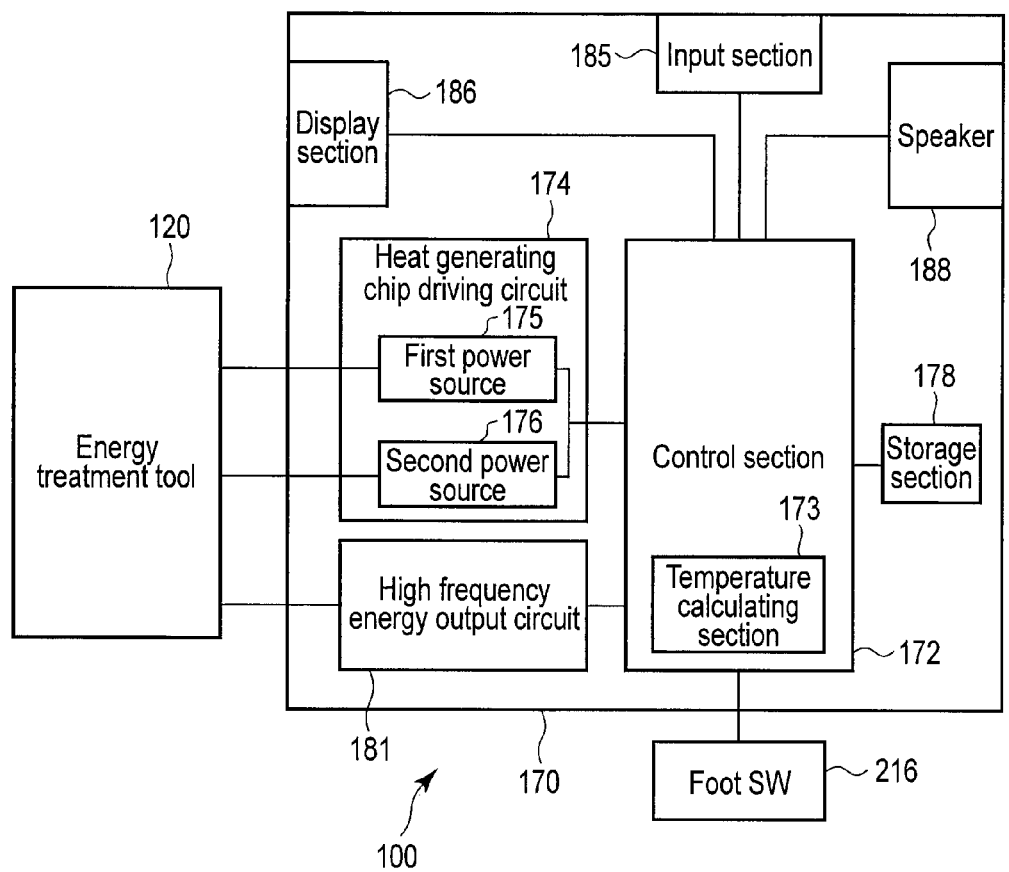
FIG. 7 is a view showing a configuration example of a controller according to the one embodiment of the present invention.

In the controller 170, as shown in FIG. 7, there are disposed a control section 172, a heat generating chip driving circuit 174, a storage section 178, a high frequency energy output circuit 181, an input section 185, a display section 186, and a speaker 188. The control section 172 is connected to each section in the controller 170, to control each section of the controller 170.

The heat generating chip driving circuit 174 has a first power source 175 and a second power source 176. The first power source 175 is connected to the heat generating chips 140 disposed in the first high frequency electrode 132 of the energy treatment tool 120. The first power source 175 drives the heat generating chips 140 under the control of the control section 172 for the purpose of heating. That is, the first power source 175 applies a first voltage V1 to the resistance patterns 143 of the heat generating chips 140 via the energization lines 162 for the heat generating chips, to supply the power. Here, the first power source 175 can change an amount of the power to be supplied to the heat generating chips 140.

Furthermore, the second power source 176 is connected to the sheet heater 150 disposed in the second high frequency electrode 134 of the energy treatment tool 120. The second power source 176 drives the sheet heater 150 under the control of the control section 172 for the purpose of the heating. That is, the second power source 176 applies a second voltage V2 to the thin film resistor 153 of the sheet heater 150 via the energization lines 163 for the sheet heater, to supply the power. Here, the second power source 176 can change an amount of the power to be supplied to the sheet heater 150.

Moreover, the heat generating chip driving circuit 174 has a function of measuring, as a first current I1, the current which flows when the voltage is applied to the heat generating chips 140. Similarly, the heat generating chip driving circuit 174 has a function of measuring, as a second current I2, the current which flows when the voltage is applied to the sheet heater 150. The heat generating chip driving circuit 174 outputs the measured current values to the control section 172.

The control section 172 has a temperature calculating section 173. The temperature calculating section 173 calculates a resistance value of the resistance patterns 143 of the heat generating chips 140 as a first resistance value R1 on the basis of the first voltage V1 and the first current I1. Similarly, the temperature calculating section 173 calculates a resistance value of the thin film resistor 153 of the sheet heater 150 as a second resistance value R2 on the basis of the second voltage V2 and the second current I2.

The resistance value of the resistance patterns 143 changes in accordance with a temperature of the resistance patterns 143. Therefore, when a relation between the temperature and the resistance value of the resistance patterns 143 is already known, the control section 172 can acquire the temperature of the resistance patterns 143 on the basis of the resistance value of the resistance patterns 143. The temperature calculating section 173 calculates the temperature of the resistance patterns 143 from the resistance value of the resistance patterns 143 on the basis of the relation between the temperature and the resistance value of the resistance patterns 143 of the heat generating chips 140. The temperature of the resistance patterns 143 is acquired on the basis of the relation between the temperature and the resistance value of the resistance patterns 143 of the heat generating chips 140, whereby a temperature sensor does not have to be separately disposed, which enables space saving design and cost decrease.

The high frequency energy output circuit 181 is connected to the energy treatment tool 120, and drives the first high frequency electrode 132 and the second high frequency electrode 134 of the energy treatment tool 120 under the control of the control section 172. That is, the high frequency energy output circuit 181 applies a high frequency voltage to the first high frequency electrode 132 and the second high frequency electrode 134 via the energization lines 268 for the high frequency electrodes.

The control section 172 is connected to the foot switch (SW) 216, and ON indicating that a treatment by the energy treatment tool 120 is to be performed and OFF indicating that the treatment is to be stopped are input from the foot switch 216. The input section 185 is input various settings and the like of the control section 172. The display section 186 displays various pieces of information of the treatment device 100 for the medical treatment under the control of the control section 172. In the storage section 178, various pieces of data required for an operation of the controller 170 are stored. The speaker 188 outputs an alarm sound or the like.

A schematic view in which a portion concerning a heating treatment is especially extracted from the above-mentioned treatment device 100 for the medical treatment is shown in FIG. 8. As shown in this drawing, the heating treatment is performed by the energy treatment tool 120 including the holding portion 125 having the first high frequency electrode 132, the second high frequency electrode 134, the heat generating chips 140 and the sheet heater 150. The control of the energy treatment tool 120 is executed by the controller 170. The controller 170 includes the control section 172 having the temperature calculating section 173, the heat generating chip driving circuit 174 having the first power source 175 and the second power source 176, and the storage section 178. The first power source 175 is connected to the heat generating chips 140 via the energization lines 162 for the heat generating chips and the cable 160, and the second power source 176 is connected to the sheet heater 150 via the energization lines 163 for the sheet heater and the cable 160. It is to be noted that the above-mentioned configuration concerning the high frequency treatment and the cutter is not necessarily required in the treatment device 100 for the medical treatment.

In this way, for example, the first high frequency electrode 132 functions as a first heat transfer portion which comes in contact with the biotissue to transfer the heat to the biotissue. For example, the second high frequency electrode 134 functions as a second heat transfer portion which moves relatively to the first heat transfer portion and holds the biotissue together with the first heat transfer portion to transfer the heat to the biotissue. For example, the heat generating chips 140 function as first resistance elements into which a power having a first power value is supplied to heat the first heat transfer portion. For example, the sheet heater 150 functions as a second resistance element into which a power having a second power value is supplied to heat the second heat transfer portion. For example, the heat generating chips 140, the heat generating chip driving circuit 174 and the temperature calculating section 173, as a whole, function as a temperature acquiring section which acquires a temperature of the first heat transfer portion as a first temperature. For example, the control section 172 functions as a control section which calculates, on the basis of the first temperature, the first power value to set the first temperature to a desired temperature, and determines the second power value corresponding to the first power value. For example, the first power source 175 functions as a first power supplying section which supplies the power having the first power value into the first resistance elements. For example, the second power source 176 functions as a second power supplying section which supplies the power having the second power value into the second resistance element.

Next, an operation of the treatment device 100 for the medical treatment according to the present embodiment will be described. An operator operates the input section of the controller 170, to set output conditions of the treatment device 100 for the medical treatment, for example, a set power of a high frequency energy output, a desired temperature by a heat energy output, a heating time, and the like in advance. The operator may individually set each value, or may select a set of the set values in accordance with an operation type.

The holding portion 125 and the shaft 224 of the energy treatment tool 120 are inserted, for example, into an abdominal cavity through the abdominal wall. The operator operates the operation knobs 232 to open and close the holding portion 125, thereby holding the biotissue of the treatment object by the first holding member 127 and the second holding member 128. At this time, the biotissue of the treatment object comes in contact with the first main surfaces of both the first high frequency electrode 132 disposed in the first holding member 127 and the second high frequency electrode 134 disposed in the second holding member 128.

When the operator holds the biotissue of the treatment object by the holding portion 125, the operator operates the foot switch 216. When the foot switch 216 is switched ON, a high frequency power of the set power set in advance is supplied from the controller 170 to the first high frequency electrode 132 and the second high frequency electrode 134 via the cable 160. The power to be supplied is, for example, from about 20 W to 80 W. As a result, the biotissue generates the heat, and the tissue is cauterized. By this cauterization, the tissue is denatured, and coagulated.

Next, the controller 170 stops the output of the high frequency energy, and then supplies the power to the heat generating chips 140 and the sheet heater 150 so that the temperature of the first high frequency electrode 132 and the second high frequency electrode 134 reaches the desired temperature as described later in detail. Here, the desired temperature is, for example, about 200° C. At this time, the current flows through the resistance patterns 143 of the heat generating chips 140 from the first power source 175 in the heat generating chip driving circuit 174 via the cable 160 and the energization lines 162 for the heat generating chips. The resistance patterns 143 of the respective heat generating chips 140 generate the heat by the current. The heat generated in the resistance patterns 143 is transferred to the first high frequency electrode 132 via the substrate 141 and the joining metal layer 149. As a result, the temperature of the first high frequency electrode 132 rises.

Similarly, the current flows through the thin film resistor 153 of the sheet heater 150 from the second power source 176 in the heat generating chip driving circuit 174 via the cable 160 and the energization lines 163 for the sheet heater. The thin film resistor 153 of the sheet heater 150 generates heat by the current. The heat generated in the thin film resistor 153 is transferred to the second high frequency electrode 134 via the substrate 151. As a result, the temperature of the second high frequency electrode 134 rises.

By the heat, the biotissue which comes in contact with the first main surface of the first high frequency electrode 132 or the second high frequency electrode 134 is further cauterized, and further coagulated. When a predetermined treatment time elapses, the output of the heat energy is stopped. Finally, the operator operates the operation knobs 232 to move the cutter 254, and cuts the biotissue. As described above, the treatment of the biotissue is completed.

In the present embodiment, the biotissue held by the first holding member 127 and the second holding member 128 has a crushed state. Therefore, a contact state of the biotissue with the first holding member 127 is substantially equal to a contact state of the biotissue with the second holding member 128. Therefore, when the material and shape of the first holding member main body 262 are the same as the material and shape of the second holding member main body 272 and the heat loads of these main bodies are equal to each other, the power to be supplied to the first holding member 127 may be equal to the power to be supplied to the second holding member 128. Consequently, in the present embodiment, during feedback control, a power P to be supplied is determined on the basis of the temperature of the heat generating chips 140, and the same power P is also supplied to the sheet heater 150.

Figure 9:
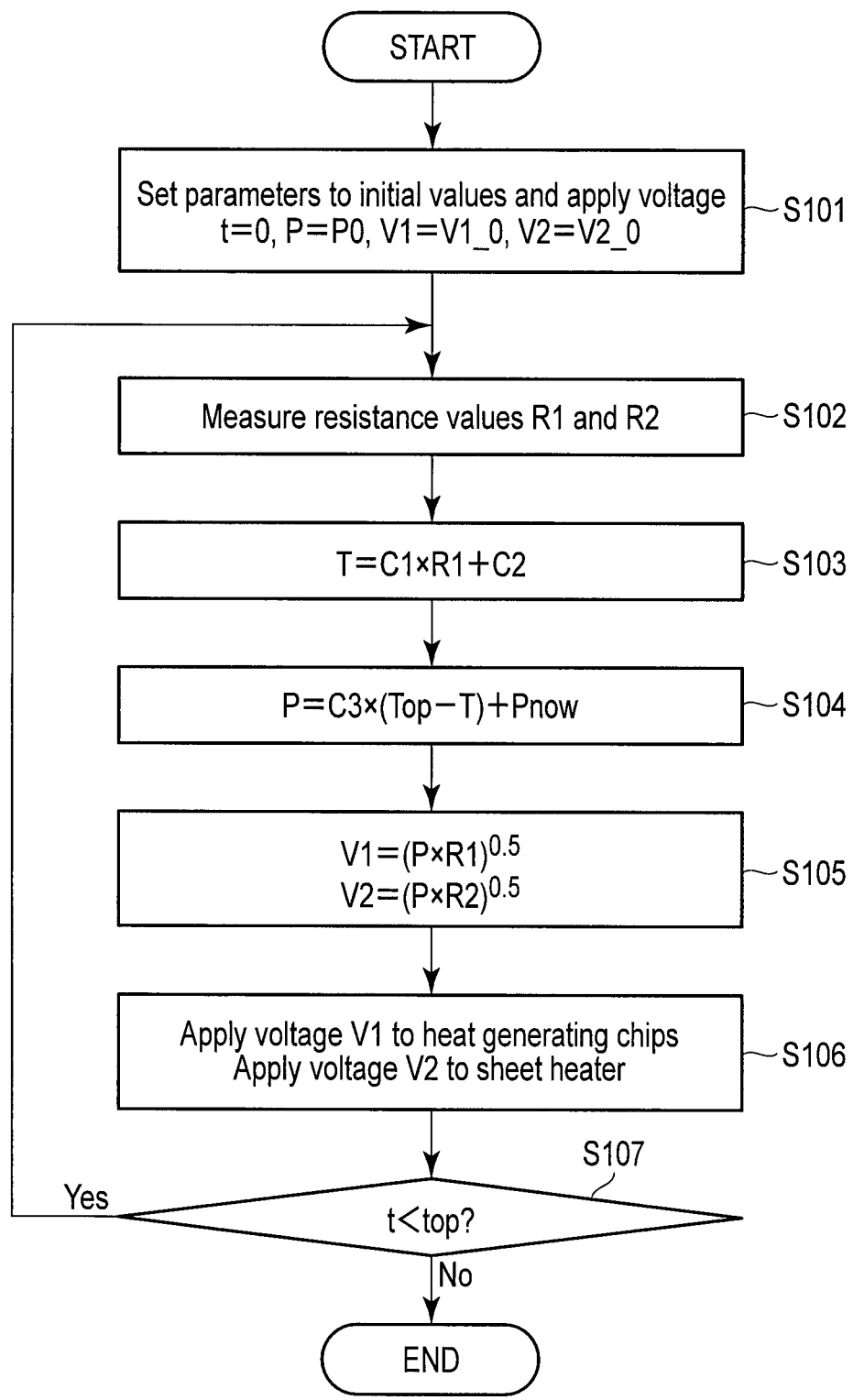
FIG. 9 is a flowchart showing one example of processing by a control section of the treatment device for the medical treatment according to the one embodiment of the present invention.

The feedback temperature control of the first high frequency electrode 132 and the second high frequency electrode 134 by the control section 172 in the present embodiment will be described with reference to a flowchart shown in FIG. 9.

In step S101, the control section 172 sets various parameters to initial values, and causes the heat generating chip driving circuit 174 to start supplying the power to the heat generating chips 140 and the sheet heater 150. For example, an elapsed time t is set to 0, the power P to be supplied is set to an initial power P0, the voltage V1 to be applied to the resistance patterns 143 of the heat generating chips 140 is set to an initial voltage V1_0, and the voltage V2 to be applied to the thin film resistor 153 of the sheet heater 150 is set to an initial voltage V2_0, respectively.

In step S102, the control section 172 causes the heat generating chip driving circuit 174 to measure the first current I1 which flows through the resistance patterns 143 of the heat generating chips 140, and the second current I2 which flows through the thin film resistor 153 of the sheet heater 150. The temperature calculating section 173 in the control section 172 calculates the resistance value R1 of the resistance patterns 143 on the basis of the first voltage V1, and a value of the first current I1 which is acquired from the heat generating chip driving circuit 174 in accordance with the following equation (1):

$$R1 = V1/I1. \tag{1}$$

Similarly, the temperature calculating section 173 in the control section 172 calculates the resistance value R2 of the thin film resistor 153 on the basis of the second voltage V2, and a value of the second current I2 flowing at this time which is acquired from the heat generating chip driving circuit 174 in accordance with the following equation (2):

$$R2 = V2/I2. \tag{2}$$

In step S103, the temperature calculating section 173 in the control section 172 calculates the temperature T of the resistance patterns 143 in accordance with the following equation (3):

$$T = C1 \times R1 + C2, \tag{3}$$

where C1 and C2 are constants corresponding to characteristics of the heat generating chips 140 that are obtained for each energy treatment tool 120. The constants C1 and C2 are stored, for example, in the memory 123. When the energy treatment tool 120 is connected to the controller 170, the constants are read, and stored, for example, in the storage section 178. The temperature calculating section 173 reads the constants C1 and C2 stored in the storage section 178, to perform the calculation by use of these constants.

In step S104, the control section 172 calculates the power P to be supplied to the resistance patterns 143 in accordance with the following equation (4):

$$P = C3 \times (\text{Top} - T) + P\text{now}, \tag{4}$$

where C3 is a control gain, and a predetermined value is given thereto. Top is a desired temperature, and Pnow is the power which is being supplied now. Here, simple proportional control in which the control gain is C3 is used, but PID control may be used to execute more stable control. The power P obtained here is supplied to the heat generating chips 140 and the sheet heater 150.

In step S105, the control section 172 calculates the first voltage V1 to be applied to the heat generating chips 140 and the second voltage V2 to be applied to the sheet heater 150 in accordance with the following equations (5) and (6):

$$V1 = (P \times R1)^{0.5}, \tag{5}$$

$$V2 = (P \times R2)^{0.5}. \tag{6}$$

Here, there is the possibility that the first resistance value R1 is different from the second resistance value R2, and hence even when the same power P is supplied, there is the possibility that the first voltage V1 is different from the second voltage V2.

In step S106, the control section 172 causes the first power source 175 of the heat generating chip driving circuit 174 to apply the first voltage V1 to the resistance patterns 143 of the heat generating chips 140. Similarly, the control section 172 causes the second power source 176 of the heat generating chip driving circuit 174 to apply the second voltage V2 to the thin film resistor 153 of the sheet heater 150.

In step S107, the control section 172 determines whether or not the elapsed time t is smaller than a treatment time top. When the elapsed time t is smaller than the treatment time top, the processing returns to the step S102. On the other hand, when the elapsed time t is the treatment time top or more, the control section 172 ends the processing. In this way, the processing of the step S102 to the step S107 is repeatedly performed until the treatment time top elapses, and the power is supplied to the energy treatment tool 120.

In the present embodiment, the biotissue held by the first holding member 127 and the second holding member 128 is crushed, for example, into about 1 mm. Therefore, it can be regarded that the contact state of the biotissue with the first holding member 127 is equal to the contact state of the biotissue with the second holding member 128. Furthermore, concerning the biotissue of a portion sandwiched between the first holding member 127 and the second holding member 128, various characteristics concerned with the temperature rise, for example, thermal conductivity, specific heat and water content ratio are substantially uniform. Furthermore, the material and shape of the first holding member main body 262 are about the same as the material and shape of the second holding member main body 272, and the heat loads of these main bodies are substantially equal to each other. As a result, even when the power to be supplied to the first holding member 127 is equal to the power to be supplied to the second holding member 128, suitable temperature control can be executed concerning the heating of the biotissue held by the first holding member 127 and the second holding member 128 at the desired temperature.

According to the present embodiment, when the relation between the resistance value and the temperature of the heat generating chips 140, i.e., the above-mentioned constants C1 and C2 are acquired in advance, it is not necessary to acquire a relation between the resistance value and the temperature of the sheet heater 150 in advance. Therefore, it is possible to cut a process of acquiring the relation between the resistance value and the temperature of the sheet heater 150. Furthermore, by the cutting of the process concerning the sheet heater 150, costs of the energy treatment tool 120 can be decreased.

It is to be noted that for the purpose of executing the temperature control with high precision, a thin film metal resistor which can stably and easily be provided with a comparatively high resistance is preferably used in the resistance patterns 143 of the heat generating chips 140. This is because when the resistance value is low, an influence of a parasitic resistor such as a lead wire remarkably appears, which deteriorates the temperature calculating precision. In contrast, for example, a heater element of a comparatively inexpensive carbon thin film can be utilized in the thin film resistor 153 of the sheet heater 150. In consequence, as compared with a case where portions equivalent to the heat generating chips 140 are used in both the first holding member 127 and the second holding member 128, the decrease of the costs of the energy treatment tool 120 can be achieved also by utilizing the sheet heater 150. Furthermore, according to the present embodiment, the structure of the device and the control of the device can be simplified, as compared with a case where, for example, the heat generating chips 140 are mounted in both the first holding member 127 and the second holding member 128, and the feedback control of the first holding member 127 is also executed in the second holding member.

Here, the heat generating member to be disposed in the first holding member 127 is different from the heat generating member to be disposed in the second holding member 128, but, for example, the same heat generating chips 140 can be used. Also in this case, the power to be supplied which is calculated on the basis of the temperature of the heat generating chips 140 disposed in the first holding member 127 is supplied to the heat generating chips disposed in the second holding member 128, which can simplify the control.

It is to be noted that in general, a power equal to that of the heat generating chips 140 is supplied to the sheet heater 150. However, when a heat capacity of the first holding member 127 is different from that of the second holding member 128, or when a joining state between each of the heat generating chips 140 and the first high frequency electrode 132 is different from a joining state between the sheet heater 150 and the second high frequency electrode 134, the power to be supplied to the sheet heater 150 can be a power calculated by applying predetermined correction to the power to be supplied to the heat generating chips 140. For example, the power to be supplied to the sheet heater 150 can be a value which is proportional to the power to be supplied to the heat generating chips 140.

In the present embodiment, the temperature of the heat generating chips 140 is acquired on the basis of the resistance value of the resistance patterns 143. However, the configuration is not limited to this example, and a temperature sensor connected to the temperature calculating section 173 may separately be disposed on the first high frequency electrode 132. In this case, the temperature sensor and the temperature calculating section 173 function as the temperature acquiring section. Also in this case, the temperature sensor may only be disposed in the first high frequency electrode 132, and does not have to be disposed in the second high frequency electrode 134. Therefore, the configuration of the energy treatment tool 120 can be simplified to cut the costs thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device for a medical treatment configured to heat a biotissue at a desired temperature to perform the medical treatment, the device comprising:
    a first heat transfer portion configured to come in contact with the biotissue to transfer heat to the biotissue;
    a second heat transfer portion configured to move relatively to the first heat transfer portion, and hold the biotissue together with the first heat transfer portion to transfer the heat to the biotissue;
    a first resistance element to which a power having a first power value is supplied to heat the first heat transfer portion;
    a second resistance element to which a power having a second power value is supplied to heat the second heat transfer portion;
    a temperature acquiring section configured to only acquire a temperature of the first heat transfer portion as a first temperature;
    a controller configured to:
        calculate the first power value to set the first temperature to the desired temperature based on the first temperature, and
        apply a predetermined correction to the first power value to determine the second power value;
    a first power supplying section configured to supply the power having the first power value to the first resistance element; and
    a second power supplying section configured to supply the power having the second power value to the second resistance element.

2. The treatment device for the medical treatment according to claim 1, wherein the temperature acquiring section acquires the first temperature based on a resistance value of the first resistance element.

3. The treatment device for the medical treatment according to claim 1, wherein the second power value is proportional to the first power value.

4. The treatment device for the medical treatment according to claim 1, wherein a heat generating portion of the first resistance element comprises a metallic thin film.

5. The treatment device for the medical treatment according to claim 1, wherein a resistance value of the first resistance element is larger than a resistance value of the second resistance element.

6. The treatment device for the medical treatment according to claim 2, wherein the second power value is proportional to the first power value.

7. The treatment device for the medical treatment according to claim 2, wherein a heat generating portion of the first resistance element comprises a metallic thin film.

8. The treatment device for the medical treatment according to claim 2, wherein a resistance value of the first resistance element is larger than a resistance value of the second resistance element.

9. The treatment device for the medical treatment according to claim 1, wherein the first resistance element is a heating generating chip with a resistance pattern formed of a metal film and the second resistance element is a sheet heater having a thin resistor using a thin film having a resistance value lower than the resistance value of the resistance pattern.

10. A treatment device for a medical treatment configured to heat a biotissue at a desired temperature to perform the medical treatment, the device comprising:
    a first heat transfer surface configured to come in contact with the biotissue to transfer heat to the biotissue;

a second heat transfer surface configured to move relatively to the first heat transfer surface, and hold the biotissue together with the first heat transfer surface to transfer the heat to the biotissue;

a first resistance heater to which a power having a first power value is supplied to heat the first heat transfer surface;

a second resistance heater to which a power having a second power value is supplied to heat the second heat transfer surface; and a processor comprising hardware, the processor configured to:

acquire a temperature of the first heat transfer surface as a first temperature;

calculate the first power value to set the first temperature to the desired temperature based on the first temperature;

determine the second power value by applying a predetermined correction to the first power value;

supply the power having the first power value to the first resistance heater; and supply the power having the second power value to the second resistance heater.

11. The treatment device for the medical treatment according to claim 10, wherein the processor acquires the first temperature based on a resistance value of the first resistance heater.

12. The treatment device for the medical treatment according to claim 10, wherein the second power value is proportional to the first power value.

13. The treatment device for the medical treatment according to claim 10, wherein the first resistance heater comprises a metallic thin film.

14. The treatment device for the medical treatment according to claim 10, wherein a resistance value of the first resistance heater is larger than a resistance value of the second resistance heater.

15. The treatment device for the medical treatment according to claim 11, wherein the second power value is proportional to the first power value.

16. The treatment device for the medical treatment according to claim 11, wherein the first resistance heater comprises a metallic thin film.

17. The treatment device for the medical treatment according to claim 11, wherein a resistance value of the first resistance heater is larger than a resistance value of the second resistance heater.

18. The treatment device for the medical treatment according to claim 10, wherein the first resistance element is a heating generating chip with a resistance pattern formed of a metal film and the second resistance element is a sheet heater having a thin resistor using a thin film having a resistance value lower than the resistance value of the resistance pattern.

* * * * *